United States Patent [19]

Su et al.

[11] Patent Number: 5,003,084
[45] Date of Patent: Mar. 26, 1991

[54] PROCESS FOR PREPARING ALKYLENE CARBONATES

[75] Inventors: Wei-Yang Su; George P. Speranza, both of Austin, Tex.

[73] Assignee: Texaco Chemical Company, White Plains, N.Y.

[21] Appl. No.: 481,929

[22] Filed: Feb. 20, 1990

[51] Int. Cl.$^5$ .................................... C07D 317/12
[52] U.S. Cl. ........................ 549/230; 549/229; 549/233; 549/518
[58] Field of Search ............... 549/229, 230, 233, 518

[56] References Cited

U.S. PATENT DOCUMENTS

| | | | |
|---|---|---|---|
| 4,009,183 | 2/1977 | Fumagalli et al. | 549/230 |
| 4,344,881 | 8/1982 | Strege et al. | 549/230 |
| 4,353,831 | 10/1982 | Strege et al. | 549/230 |

FOREIGN PATENT DOCUMENTS 0689705  4/1953  European Pat. Off. ............ 549/230

*Primary Examiner*—Mukund J. Shah
*Assistant Examiner*—Y. N. Gupta
*Attorney, Agent, or Firm*—Jack H. Park; Kenneth R. Priem; Cynthia L. Kendrick

[57] ABSTRACT

Disclosed is a process for preparing alkylene carbonates which comprises reacting the corresponding alkylene glycol and urea, optionally in the presence of a catalyst comprising a tin-containing compound, and represented by the equation:

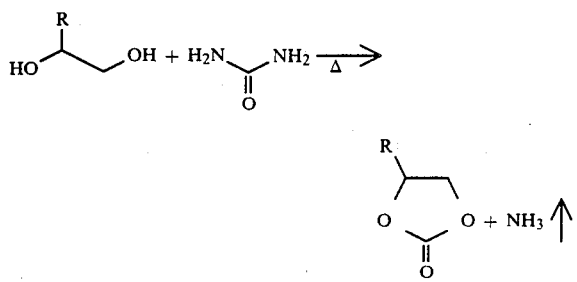

where R represents an alkyl group containing 1 to 16 carbons.

17 Claims, No Drawings

PROCESS FOR PREPARING ALKYLENE CARBONATES

FIELD OF THE INVENTION

The present invention relates to the production of alkylene carbonates.

More specifically this invention relates to a novel process for the preparation of alkylene carbonates, such as 1,2-butylene carbonate, from the corresponding alkylene glycol and urea. For example, 1,2-butanediol and urea are reacted in the presence of nitrogen and, optionally, in the presence of a tin catalyst to prepare 1,2-butylene carbonate.

The invention is particularly advantageous in its simplicity, use of mild conditions, low cost of starting materials and optional requirement for a catalyst.

BACKGROUND OF THE INVENTION

Methods of preparing alkylene carbonates are known in the art, however the methods used in the past generally involved rather indirect routes and expensive reactants and often employed reaction mechanisms which were susceptible to steric hindrances.

U.S. Pat. No. 2,773,070 describes one of the earlier methods of preparing alkylene carbonates which comprises reacting an alkylene oxide with a molar excess of carbon dioxide at a temperature between 100° C. and 225° C. and a pressure in excess of 300 psig in the presence of a catalyst comprising one of a specified group of ammonium halides.

Early art in the field indicates that cyclic carbonate esters of 1,2-diols can be reacted with thiocyanate salts in the synthesis of episulfides, however the reaction was found to be quite susceptible to steric hindrance. See *J. Org. Chem.* (1962), 27, 2832.

An article in *J. Am. Chem. Soc.* (1962) 84, 747 discusses, among other things, the high-resolution proton nuclear magnetic resonance spectra which were determined for the isomers of the cyclic carbonate of 2,3-butanediol. Chemical shifts and coupling constants for the compounds are shown.

There is disclosed in U.S. Pat. No. 3,025,305 a process for the production of cyclic carbonates which comprises reacting a monoolefin of about 2 to about 30 carbon atoms with carbon dioxide having a partial pressure of at least about 500 psig and a molecular oxygen-containing gas at a temperature of about 200° to 400° F. and a total pressure sufficient to maintain the liquid phase using two catalysts, a cobalt organic salt and a type of quaternary ammonium compound.

In U.S. Pat. No. 3,923,842 there is disclosed a process for the preparation of an oxirane compound from the corresponding olefin. Here a vicinal halohydrin is formed by reacting the corresponding olefin with oxygen in the presence of an iron halide and a copper halide, under reaction conditions where iron oxide is formed as a coproduct, and is reacted with an amine and carbon dioxide to form one of a group of identified cyclic carbonate esters.

In U.S. Pat. No. 4,009,183 there is disclosed a process for preparing alkylene carbonates from olefins reacted with carbon dioxide in the presence of iodine or certain iodine-containing compounds and an oxygen conveyor at a temperature between 30° and 120° C. and at a pressure between atmospheric to 100 atmospheres and a pH value between 3 and 8.

In U.S. Pat. No. 4,224,223 there is described a process for the preparation of a cyclic alkylene carbonate ester which comprises reacting a cyclic or linear olefin having from 2 to 15 carbon atoms in liquid phase in the presence of oxygen or an oxygen-containing gas and a catalytic amount of an iodine or iodide of a metal and a catalytic iron or copper compound or mixture thereof with carbon dioxide at a temperature of from 50° to 160° C. at a total pressure of from 200 to about 2000 psig and a pH value of between about 4 and 8.

Venturello and D'Aloisio have described a method of preparing 1,2-alkanediyl carbonates in high yields in short reaction times under mild conditions without the drawbacks of toxic or hazardous reagents or high temperatures or the formation of undesired glycols which are hard to separate from cyclic carbonates. This method comprises stirring the corresponding vic-halohydrins with tetramethyl ammonium hydrogen carbonate in acetonitrile. See "A Convenient Synthesis of 1,2-Alkanediyl Carbonates." *Synthesis* (1985), 1, 33.

In DE 3723782C (Dainippon Ink Chem KK) cyclocarbonates are prepared from a vicinal halo-hydrin and alkali bicarbonates by heating in aprotic organic solvents such as dimethyl sulfoxide, acetonitrile and dimethylformamide.

From the available art it does not appear that any skilled in the art have heretofore considered a method for preparing alkylene carbonates, especially 1,2-butylene carbonate, from the corresponding alkylene glycol and urea. In the instant invention it has been surprisingly discovered that 1,2-butanediol and urea can be reacted in the presence of, optionally, a tin catalyst to prepare 1,2-butylene carbonate. This process should constitute a very desirable advance in the field because it is comparatively simple, the starting materials are relatively cheap and mild conditions can be employed.

SUMMARY OF THE INVENTION

This invention concerns a novel process for the production of alkylene carbonates from the reaction of the corresponding alkylene glycol and urea, optionally in the presence of a tin catalyst at atmospheric pressure and a temperature of from about 130° C. to 200° C.

The process demonstrates a conversion of glycol as high as 95% and a selectivity for the alkylene carbonate as high as 96%. In addition, this process would be very attractive commercially by virtue of its use of less expensive and less hazardous reactants, mild conditions and the efficiency of the process.

DETAILED DESCRIPTION OF THE INVENTION

In accordance with the present invention, an alkylene glycol having about 3 to 18 carbon atoms is reacted with urea in the presence of nitrogen to produce an alkylene carbonate. The reaction can be represented by the following equation:

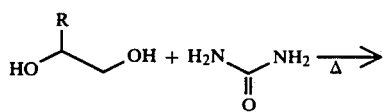

-continued

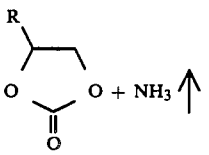

where R represents an alkyl group containing 1 to 16 carbons.

The alkylene glycol can be selected from the group of alkylene glycols having the following structures:

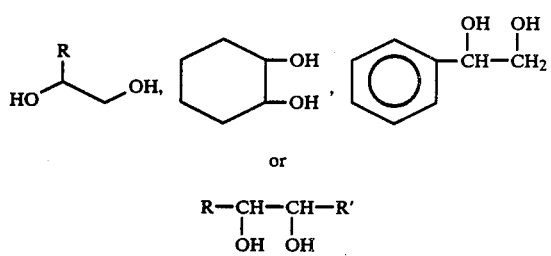

where R is an alkyl group containing 1 to 16 carbon atoms and R' is H or an alkyl group containing 1 to 8 carbons. Suitable alkylene glycols included in this group are cyclohexane diols, aryl-aliphatic 1,2 diols and internal 1,2 glycols.

Vicinal glycols having the structure:

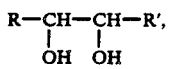

can be used wherein R and R' are defined as above and suitable examples include 1,2-cyclohexane diol and styrene glycol.

In most examples the alkylene glycol is represented by the structure:

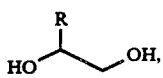

where R is an alkyl group containing 1 to 16 carbon atoms. Preferably the alkylene glycol will contain about 3 to 8 carbon atoms. One group of reactants which are effective are 1,2-diols. Examples of suitable 1,2-diols include 1,2-butanediol, 1,2-propanediol, 1,2-hexanediol, cyclohexane 1,2-diol and 1,2-styrene diol. Good results were observed when R was methyl or ethyl as in the case of 1,2-propanediol or 1,2-butanediol. It is worth noting that greater polarity of the alkylene glycol seems to have an adverse effect on selectivity. The reaction proceeds more efficiently with 1,2-butylene glycol than 1,2-propylene glycol which in turn is preferred over 1,2-ethylene glycol.

A solvent is not necessary to carry out the process of the invention, however the reaction can be run in the presence of a polar aprotic solvent. Polar aprotic solvents include acetonitrile, dimethylformamide, dimethylacetamide, dimethylsulfoxide, diethylformamide and diethylacetamide. The preferred polar aprotic solvents are amides such as dimethyl acetamide and dimethylformamide.

The process works well without a catalyst, however a catalyst containing tin may be used and is demonstrated in Example 2. Suitable tin-containing compounds which may be used as the catalyst include the dialkyl tin dicarboxylates and tin salts of organic carboxylic acids. Good results were observed using the commercially available tin catalyst T-12. T-12 is dibutyl tin dilaurate and is manufactured by M and T Chemicals. Where the catalyst was used the ratio of reactants to catalyst was not critical.

Reaction conditions are generally mild, but can vary according to starting materials. Preferably, the process of the invention is conducted at atmospheric pressure. The process can be adapted so the reaction can be run under pressure as long as some method is available for eliminating the ammonia. Where the reaction is conducted under pressure, however it would be particularly undesirable for the pressure to exceed 500 psig. Preferably the process of the invention is conducted at relatively mild temperatures. Generally the temperature range is from about 100° C. to 250° C. The preferred temperature range is from about 130° C. to 200° C. As demonstrated in the examples, good results were observed using temperatures in the range of 170° C.–180° C.

The preferred residence time is in the range of 1 to 5 hours.

The alkylene glycol/urea ratios may be those required by the stoichiometry of the reaction, but they may also vary within rather wide intervals.

Generally, the amount of alkylene glycol employed is in the range of 1 to 5 moles of glycol group per 1 to 5 moles of urea. Where a ratio in the range of 2 moles of urea per mole of 1,2-butanediol was used (Example 3) a 95% conversion of 1,2-butanediol and 96% selectivity for 1,2-butylene carbonate was observed.

According to this invention alkylene glycol and urea are introduced into the reaction vessel. The reaction mixture was heated up to the desired temperature and the ammonia was released from the reaction. The desired products of this process according to the invention are alkylene carbonates, especially 1,2-propanediol and 1,2-butanediol.

Products have been identified in this work by gas chromatography (gc) or NMR or a combination of these techniques. Analyses have, for the most part, been by g.c.; all temperatures are in degrees centigrade and all pressures in pounds per square inch gauge.

The following examples illustrate the novel process of this invention. The examples are only for illustrating the invention and are not to be considered limitative.

EXAMPLE 1

To a 500-ml three-necked flask equipped with a thermometer, condenser, stirrer and nitrogen inlet was charged 60 g (1 mole) of urea and 90 g (1 mole) of 1,2-butanediol. The reaction was carried out at 170° C. with stirring for three hours. Ammonia released from the reaction was noted. About 122.9 g of reaction mixture was recovered. GC and NMR analyses showed that a 99% selectivity of 1,2-butylene carbonate was obtained with 48% 1,2-butanediol conversion.

EXAMPLE 2

The procedure of Example 1 was followed except 1.5 g of T-12 catalyst (Tin catalyst) was also charged. About 110 g of reaction mixture was recovered. GC and NMR analyses showed that 99% selectivity of 1,2-butylene carbonate was obtained with 64% conversion of 1,2-butanediol.

EXAMPLE 3

The procedure of Example 1 was followed except that 120 g of urea was charged. About 137 g of reaction mixture was recovered. GC and NMR analyses showed that a 96% selectivity of 1,2,-butylene carbonate and a 4% selectivity of 5-ethyl-2-oxazolidinone were obtained with 95% conversion of 1,2-butanediol.

EXAMPLE 4

The procedure of Example 1 was followed except that 180 g of 1,2-butanediol was charged. About 206.4 g of reaction mixture was recovered. GC and NMR analyses showed that a 94% selectivity of 1,2-butylene carbonate was obtained with 33% 1,2-butanediol conversion.

EXAMPLE 5

The procedure of Example 1 was followed except that 102 g of 1,2-propanediol was charged. About 123.5 g of reaction mixture was recovered. GC and NMR analyses showed that an 84% selectivity of propylene carbonate was obtained with 43% conversion of 1,2-propanediol.

EXAMPLE 6

To a 500-ml three-necked flask equipped with a thermometer, condenser, stirrer and nitrogen inlet was charged 61.3 g of urea and 118.6 g of hexylene glycol, a 1,3-diol. The reaction was carried out at 170°–180° C. for three hours. The reaction gave very poor selectivity and conversion. This demonstrates that 1,3-diols do not work well in our invention.

What is claimed is:

1. A process for the preparation of alkylene carbonates which comprises reacting alkylene glycols and urea.

2. The process of claim 1 wherein the alkylene glycol is selected from the group of alkylene glycols having the structures:

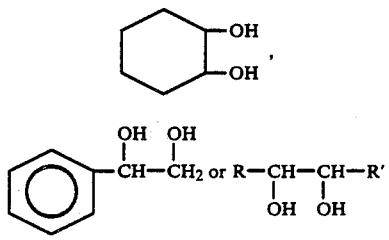

where R is an alkyl group containing 1 to 16 carbon atoms and R' is H or an alkyl group containing 1 to 8 carbon atoms.

3. The process of claim 2 wherein the alkylene glycols are selected from the group consisting of cyclohexane diols, aryl-aliphatic 1,2-diols and internal 1,2-glycols.

4. The process of claim 2 wherein the alkylene glycol is a vicinal glycol having the formula:

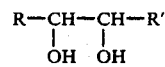

where R is an alkyl group containing 1 to 16 carbon atoms and R' is H or an alkyl group containing 1 to 8 carbons.

5. The process of claim 4 wherein the vicinal glycol is selected from the group consisting of 1,2-cyclohexane diol and styrene glycol.

6. The process of claim 1 wherein the alkylene glycol has the formula:

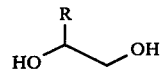

where R is an alkyl group containing 1 to 16 carbon atoms.

7. The process of claim 6 wherein the alkylene glycol has the formula:

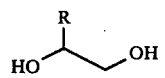

where R is an alkyl group containing 1 to 6 carbon atoms.

8. The process of claim 6 wherein the alkylene glycol is selected from the group consisting of 1,2-butanediol, 1,2-propanediol, 1,2-hexandiol, cyclohexane 1,2-diol and 1,2-styrene diol.

9. The process of claim 7 wherein the alkylene glycol is 1,2-butanediol.

10. The process of claim 8 wherein the alkylene glycol is 1,2-propanediol.

11. The process of claim 1 further comprising the optional use of a catalyst consisting of a tin-containing compound.

12. The process of claim 11 wherein a tin-containing compound is used as a catalyst and is selected from the group consisting of dialkyl tin dicarboxylates and tin salts of organic carboxylic acids.

13. The process of claim 12 wherein the catalyst comprises dibutyl tin dilaurate.

14. The process of claim 1 wherein the pressure is atmospheric.

15. The process of claim 1 wherein the pressure is in the range 0 to 500 psig.

16. The process of claim 15 further comprising a method of eliminating the ammonia by-product.

17. The process of claim 1 wherein the temperature is from 130° C. to 200° C.

* * * * *